United States Patent
Weber et al.

(10) Patent No.: US 6,432,101 B1
(45) Date of Patent: Aug. 13, 2002

(54) SURGICAL DEVICE FOR PERFORMING FACE-LIFTING USING ELECTROMAGNETIC RADIATION

(75) Inventors: Paul J. Weber, Fort Lauderdale, FL (US); Luiz B. DaSilva, Danville, CA (US); Michael Robert Weber, Clearwater, FL (US)

(73) Assignee: Pearl Technology Holdings, LLC, Tampa, FL (US)

(*) Notice: Subject to any disclaimer, the term of this patent is extended or adjusted under 35 U.S.C. 154(b) by 0 days.

(21) Appl. No.: 09/478,172

(22) Filed: Jan. 5, 2000

Related U.S. Application Data

(63) Continuation-in-part of application No. 09/085,948, filed on May 28, 1998, now Pat. No. 6,203,540.

(51) Int. Cl.[7] .............................................. A61B 18/18
(52) U.S. Cl. ................................................ 606/2; 606/9
(58) Field of Search ...................... 606/2–4, 9–11, 606/13, 15, 16, 27, 28, 32, 34, 40, 41, 49, 169; 604/22, 35, 19; 601/2

(56) References Cited

U.S. PATENT DOCUMENTS

| | | | | |
|---|---|---|---|---|
| 4,537,791 A | * | 8/1985 | Tarjan | 427/2 |
| 5,246,436 A | * | 9/1993 | Rowe | 606/13 |
| 5,500,012 A | * | 3/1996 | Brucker et al. | 607/122 |
| 5,693,043 A | * | 12/1997 | Kittrell et al. | 606/15 |
| 5,776,092 A | * | 7/1998 | Farin et al. | 604/22 |
| 6,203,540 B1 | * | 3/2001 | Weber | 606/15 |

OTHER PUBLICATIONS

P.J. Weber et al, Bulbous–Lysing Underminers, J. Dermatol Surg. Oncol., 15:12, Dec. 1989, pp. 1251–1253.

* cited by examiner

*Primary Examiner*—Michael Peffley
*Assistant Examiner*—Pete J Vrettakos
(74) *Attorney, Agent, or Firm*—John P. Wooldridge

(57) ABSTRACT

A device is described that can be used by surgeons to provide quick and accurate face-lifting maneuvers that minimize the amount of tissue that has to be removed. The device comprises of a hollow undermining shaft with specially designed tip that can safely separate tissue planes and lyse fibrous tissue. Laser light can be delivered down the shaft to heat and cause tissue contraction. Device can also include a temperature sensor that can be used to control laser power. Optionally the device can also use ultrasound or electrosurgical energy to improve tissue lysing.

25 Claims, 3 Drawing Sheets

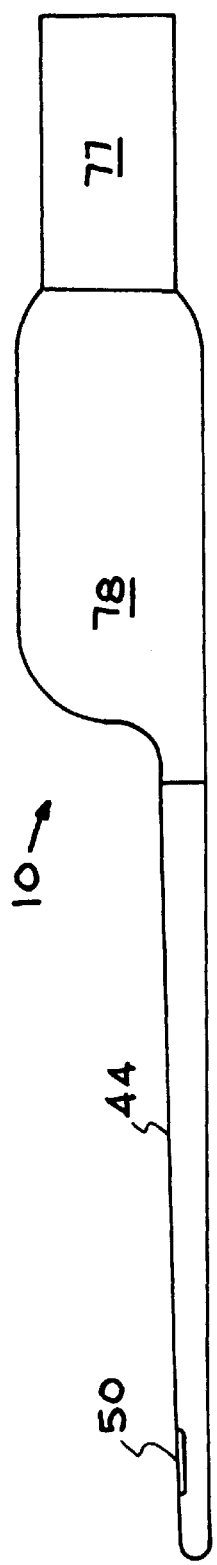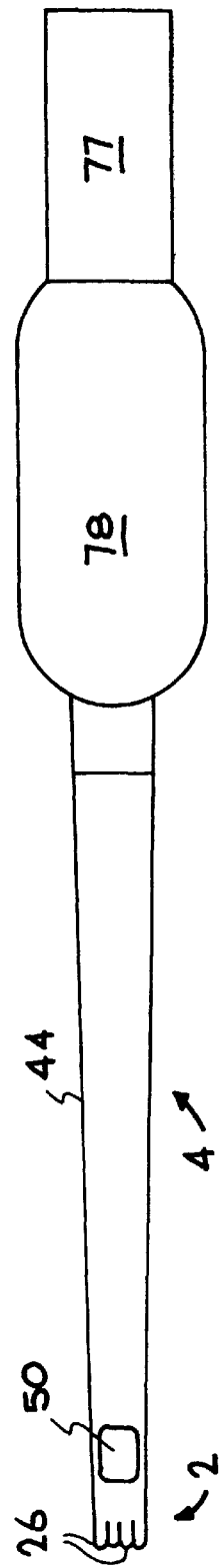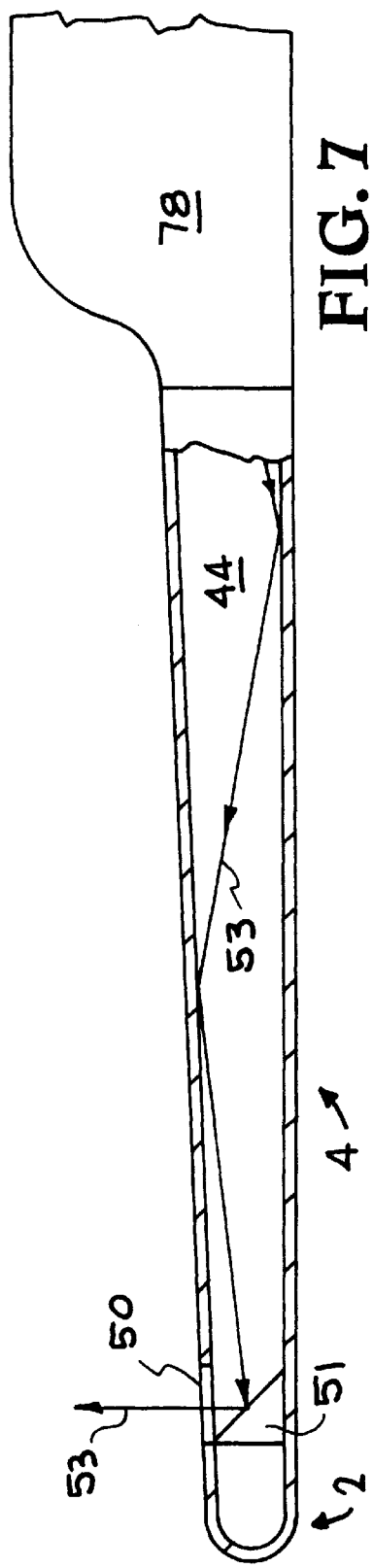

SURGICAL DEVICE FOR PERFORMING FACE-LIFTING USING ELECTROMAGNETIC RADIATION

This application is a continuation-in-part of U.S. patent application Ser. No. 09/085,948, filed May 28, 1998, now U.S. Pat. No. 6,203,540.

BACKGROUND OF THE INVENTION

1. Field of the Invention

This invention relates to a surgical device for performing face-lifting using electromagnetic radiation, and more particularly to a device with a specialized tip design that delivers laser light and optionally ultrasonic energy. The invention provides a surgical device that can improve the accuracy and speed of face-lift operations. Use of the present invention may controllably cause thermally related healing contraction of the target tissues thus allowing face lifting in younger patients without the removal or cutting-out of skin in properly selected patients.

2. Description of Related Art

Critical Anatomy and Nomenclature:

Definitions:

Cutting (in surgery) will be defined as relatively cleanly breaking through similar or dissimilar tissues with minimal adjacent tissue trauma and thus little tissue stretching, tearing or ripping. Lysis (in surgery) will be defined as breaking through similar or dissimilar tissues with or without adjacent tissue trauma and may involve stretching, tearing or ripping. Depending upon the tissues lysed, the degree of stretching or tearing of lysed tissue edges may be inconsequential or may even result in a desirable benefit such as post surgical contraction. Planes of tissue are not often flat and represent the curviform intersection of dissimilar tissues and are made at least partly of fibrous tissues, either loose and spongy or firm and tough. Planes between the soft internal organs are usually loose and spongy. Planes of tissues in the face and on bones are firm and tough. Undermining will be defined as tissue separation either within or between defined tissue planes. Undermining may be sharp (instrument) or dull (instrument) depending upon the amount of fibrous tissue binding or existing between the tissue planes to be separated. Undermining is usually performed, as is most surgery, with the intention of minimizing trauma. Sharp instrument undermining is usually performed to separate highly fibrous or collagenous tissues, however sharp undermining suffers from the risk of penetrating adjacent tissues inadvertently because of loss of ability to follow the desired plane. Inability to follow or maintain the plane in sharp undermining is frequently due to limited visibility, difficulty "feeling" the fibrous plane, or scarring (collagen fibrosis) resulting from previous trauma or surgery. Even experienced surgeons may from time to time lose the correct plane of sharp undermining; great skill is required. Blunt undermining allows a rounded, non-sharp tipped, instrument or even human finger to find the path of least resistance between tissues; once the desired plane is found by the surgeon, it is easy to maintain the plane of blunt undermining until the task is complete. Unfortunately, blunt undermining between highly fibrous tissues such as the human face usually causes tunneling with thick fibrous walls. Dissection usually implies sorting out and identification of tissues and usually implies that some sort of undermining has been performed to isolate the desired structure(s). In face-lifting surgery, plastic surgeons have so commonly used the terms undermining and dissection interchangeably that they have become synonymous in this specific situation. Tracking means to maintain a direction of movement upon forcing a tissue separating instrument without unpredictable movement or leaving the desired tissue plane(s). Planar tracking means to stay in the same tissue planes. Linear tracking means to move uniformly in a straight or uniformly curved path without unpredictable movement. Groups of linear tracks may form a network that creates an undermined tissue plane.

Anatomical Perspective: Lysis or undermining in one dimension (linear=x) implies forming a tunnel. Lysing or undermining in 2 dimensions at any one instant forms a plane (x,y). Traditional face-lift undermining is done just under the leather (dermis) layer of the skin where dermis joins underlying fat (or subcutaneous, "SQ"). Even deeper within the SQ fat run larger blood vessels and delicate, non-regenerating motor nerves to the muscles that give the human face motion and expression. Deep/beneath to the SQ fat reside the muscles and glands of the face. The relevant face-lift anatomy may be referenced in {Micheli-Pellegrini V. Surgical Anatomy and Dynamics in Face Lifts. Facial Plastic Surgery. 1992:8:1–10. and Gosain AK et al. Surgical Anatomy of the SMAS: a reinvestigation. Plast Reconstr Surg. 1993: 92:1254–1263. and Jost G, Lamouche G. SMAS in rhytidectomy. Aesthetic Plast Surg 6:69, 1982.} The SQ fat differs from body location to body location. On the face, the SQ fat has many fiber-bundles (septae) carrying nerves and blood vessels. If a surgeon were to move, shove, or forwardly-push a blunt, dull-tipped, 1-inch chisel or pencil shaped device through the fat of the face where SQ abuts the dermis, the sheer thickness of the fiber bundles would likely cause slippage of the device and result in the formation of pockets or tunnels surrounded by compacted fiber bundles or septae. Proper performance of a face-lift involves breaking the septae at a proper level to avoid damaging more important structures such as blood vessels and nerves and glands.

Disadvantages of the current techniques are numerous. Face-lifting devices described in the prior art resemble undermining devices that were constructed with cutting edges that rely entirely on the skill of the surgeon to maintain control. Inadvertent lateral cutting or tissue trauma may be difficult to control. In addition, speed of separation is effected to ensure accuracy by the surgeon in separating fibrous tissue planes. There are two principle locations for face lift undermining (dissection): in the more common lower facelift (cheek/neck-lift) undermining in the subcutaneous tissues is customarily performed; in the less common upper facelift (which approximates brow-lifting) undermining in the subgaleal or temporalis fascia plane is customarily performed. Use of prior art undermining devices (including scissors, sharp rhytisectors, etc) in these planes during cosmetic surgery has, at times, resulted in unwanted cutting, trauma or perforation of adjacent structures. Scissors and rhytisectors are planar cutting instruments; thus, the position of the cutting edges with respect to the surface of the face is controllable only by the surgeon estimating location as no $3^{rd}$ dimensional bulbous limitation exists. Unfortunately, scissors with 3 dimensionally "bulbous", rounded tips can not close all the way to cut target tissue. Scissors with 2 dimensionally rounded tips can close all the way to cut target tissue but may wander inadvertently between tissue planes due to the thin third dimension (thickness) of the scissors blades.

Rubin (U.S. Pat. No. 3,667,470) describe a bone shaver and grooving device which consists of a single sharp edged extension protruding perpendicular to the plane of motion of the cutting edge of the device. The extension is intended to carve and maintain a groove in rigid, immobile, bone as it is driven forward by a surgeon's hammer. This device is impractical for lysing facial planes because the extension would severely damage blood vessels and delicate nerves. In addition, Rubin" invetion would not maintain a planar track in soft tissues. Hendel (U.S. Pat. No. 4,600,005) describes a guided osteotome for harvesting cranial bone graft that has a single cutting tip between two bulb like guides at the edges. The guides prevent the hammer driven cutting edge from penetrating the skull too deeply as the harvesting cutting edge would tend to "dive" deep into the skull toward brain tissue if unhindered (vertical tracking control). However, these single guides with their geometry can not effectively compress or pass through the collagenous, fibrous tissues into recessions making for a more precise lysis of the grouped fibers and bundles.

Current face-lifting instruments that cut with other than manual energy do not address the novel concept of a "protected plane" during energized face-lifting dissection. Current lasers must be fired from positions outside the patient to energize tissue within the face to cut in a very imprecise fashion (reference: in *Manual of Tumescent Liposculpture and Laser Cosmetic Surgery* by Cook R C and Cook K K, Lippincott, Williams, and Wilkins, Philadelphia ISBN: 0-7817-1987-9, 1999). Tissue is damaged with little control. Current electrosurgical devices for face-lift tissue energizing must be delivered through large open pockets or through the limited access and slow moving, tedious endoscopes. Farin (U.S. Pat. No. 5,776,092) describes a single tube device that can deliver laser, ultrasound or radio frequency devices to treat tissue. However, Farin's device is not intended for separating tissue planes and is suceptible to catching, tearing or puncturing the tissue when manipulated. It would be advantageous to provide a safe harbor for the precise application of energy to proper face-lift tissues to be separated and energized while excluding vital structures such as nerves and delicate vessels and maintaining an exact distance from the very delicate surface of the skin. It would be additionally advantageous for the same provisions to allow for a uniform forward tracking and feel of motion of the device that provides a surgeon with instantaneous knowledge. Properly sized and placed protrusions and recessions address all of these problems in a manner not previously possible.

One of the most recent competing procedures to incompletely dissect/lyse/cut a face-lift plane is traditional or ultrasonic liposuction. Unfortunately, dissection is incomplete as the cannulas only make tunnels. The tissues between the tunnels must be cut with scissors in order to create a plane. When the scissors cuts the fiber tissues and blood vessels constituting the walls of the tunnels, bleeding and trauma occur and frequently require spot coagulation under visualization. Other severe drawbacks of the incomplete undermining that liposuction cannulas perform is the common trauma and resultant mouth droop paralysis that occurs in the hands of even prominent surgeons when the delicate and anatomically unpredictable (20% of the population) marginal mandibular nerve is cut. Additionally, ultrasonic cannulas become hot and can cause thermal bums called "end hits" when the cannula tip is thrust against the inside of the skin as is common during the procedure.

Just as sharp undermining or dissection has its disadvantages, as previously mentioned, blunt dissection suffers from its own difficulties as well. Forcing a blunt object through tissue avoids indiscriminate sharp cutting of important structures (nerves, vessels). Blunt undermining compacts the stronger, firmer, strands of collagen even contained within tissues as soft fat into thicker "bands" (some overly thick for uniform cutting). Undesirably for a face-lift, traditional blunt object undermining may indiscreminantely force aside and compact septae causing incomplete lysis or freeing of the tissues. Also unfortunately for face-lifting, traditional purely blunt object undermining will result in random motion or uncontrollable-slippage of the underminer tip on forward motion and thusly loss of precise tracking of the underminer through target tissue.

Currently it takes surgeons between 20 minutes and one hour to dissect/undermine/lyse/lift a lower face. It usually takes between 10 minutes and 30 minutes, depending upon the patient to spot coagulate/seal all of the blood vessels that were cut during the aforementioned lysing portion of the face-lift. For upper face-lifting times are less than half that mentioned for lower face-lifting. The present invention would reduce time for a surgeon to do both the duties of lysing and coagulation since the device performs both tasks as well as aids in maintaining proper positioning and tracking. The time reduction should be at least 50–75%. Reduced operating time means less time a wound is open to potential infection, lowered surgical costs and less time and therefore less risk under anesthesia and thus a general improvement in the procedure.

There exists a special subset of the general population that may benefit uniquely from the present invention. Men and women between the ages of 45 and 55 are just beginning to droop and develop folds. However, there is not much undulating wrinkling as in older patients. Currently long incisions of 10–20 cm are made around each of the two ears, for the purposes of hiding the scars. Skin is cut out and discarded and the remaining skin stretched. Skin does not thicken in response to stretching; it only thins. Unfortunately, some plastic surgeons in the early 1990's advocated "prophylactic" or "preemptive" face-lifting on women in their 40's purportedly to "stay ahead of nature." This philosophy has now been discounted and discredited by the vast majority of reputable experts. With the present invention, tightening will be most dramatic in younger patients between 45 and 55 years of age such that surgeons may not have to cut-out or stretch skin for a desirable effect for most patients in this population. In this case, the present invention is inserted through only 3 relatively small incisions of less than 1 cm each and energy is applied to the upper subcutaneous, lower dermal and platysmal face-lift layers. If the 3 small incisions can be used and no skin excised then the procedure will take less than 15 minutes following anesthesia and the effects will last for at least several years.

Given the disadvantages and deficiencies of current face-lifting techniques a need exists for a device that provides a fast and safe alternative. The present invention combines a unique lysing design with laser irradiation to efficiently lyse and simultaneously induce the thermal contraction necessary for face-lifting. The present invention provides a process for human face-lifting, which can be used in hospitals as well as office-based surgery and minimizes pain and risk of injury.

It is, therefore, an object of the present invention to provide an undermining device that can position lysing surfaces at a proper level for fibrous tissue lysing during a face-lift. It is a further object of the invention to provide quick and accurate face-lifting maneuvers. It is yet a further object of the invention to provide a surgical face-lifting device that easily maintains the proper dissection plane. Additionally, it has been shown that thermal effects to the collagenous (dermal, superficial platysma musculature and other) tissues of the face in the facelift plane can cause cosmetically desirable contraction of the dermal tissues with beneficial tightening of the facial tissues.

SUMMARY OF THE INVENTION

The object of the present invention is to provide a method and a device that can be used by surgeons to provide quick and accurate face-lifting maneuvers that minimize the amount of tissue that has to be removed. The device is comprised of a hollow undermining shaft with a special tip that can be easily positioned between dissection planes in tissue and then manipulated to separate tissue planes and lyse fibrous tissue. A laser light source and delivering means which delivers energy to the distal end of the shaft, a temperature sensor that monitors the tissue temperature, and control electronics that process temperature information to control the laser power for optimum tissue contraction. An optional secondary light source that is visible to the surgeon can be used to help visualize the location of the laser exit window. Optionally the device can also use ultrasound energy delivered down the shaft to improve tissue lysing.

It is a further object of the invention to provide a surgical face-lifting device that easily maintains the proper dissection plane while lysing and delivers laser energy to the internal collagenous tissues of the face to induce skin tightening.

In the preferred embodiment of the invention, the user sets the desired tissue temperature on an external control unit using a touch pad or other user interface. The shaft of the device is then inserted through a small (~1 cm long) incision and positioned at the desired tissue plane. For lower face-lifting the surgeon incises the skin in front of the ears and under the chin. Force is then applied to the shaft of the device by the users hand to separate tissue planes while excluding critical structures (nerves, vessels) thus avoiding entanglement or trauma or indiscriminate cutting of these important structures. The same protrusions that exclude critical structures by virtue of their relationship to the cutting recessed segments also serve to position the depth of the present invention with respect to the lower dermis. The spacing of the protrusions (bulbs) and recessions (lysing segments) maintains the tracking of the instrument. Tracking is instantly palpable by the surgeon and requires no monitor to know how the device is moving. Both the number and spacing of protrusions in the present invention reduce wobble or lateral (horizontal) slippage during forward thrusting of the shaft. Uniquely vertical slippage is prohibited as well. The width of the protrusions/bulbs maintains the correct distance between the lysing segments and the delicate underside of the superficial skin or dermis. The tip of the device and the action of the device can be felt/ appreciated without direct visualization (endoscope). The surgeon can palpably feel the device is tracking in the proper location. The feel of the device as it moves with palpable and easily grade-able resistance through the facial tissues can immediately tell the user the location and the amount of undermining that has occurred at that location.

The unique tip is comprised of alternating, but relatively symmetrical-across-a-midline, protrusions and recessions. The protrusions can be bulbous, geometric, etc. as long as the tips of the protrusions are able to push and compress tissues into the cutting recessed segments. The recessed segments have a sharpened edge which effectively lyses the tissue that comes into contact as the device is pushed forward. The close spacing of the grooves (caused by the alternation of tip protrusions and recessions) provides the user with a feel during forced tissue movement and signifi-cantly limits slippage. Again, the tip of the device, and the action of the device can be felt/appreciated without direct visualization (endoscope).

If desired by the user, laser light is transmitted from the laser to the hand piece and down the shaft and exits an optical window near the distal end of the shaft to heat the tissue which lies near the window. The laser light propagates away from the face to effectively heat the skin layer from the inside out. By selecting an appropriate laser wavelength, the laser penetration depth can be adjusted to control the thickness of heated tissue. For skin tightening, a $CO_2$ laser with a wavelength of 10 $\mu$m will deliver good results, other possible lasers include Er:Yag, Ho:Yag, and Nd:Yag. The purpose of the laser energy is to alter/irritate the collagen so as to controllably cause later shrinkage and to optionally to control any bleeding. Since most preferred laser sources are invisible to the human eye the device will offer the user the option to simultaneously transmit visible light down the shaft to give the user the ability to visualize the region being treated. For example, red light that is easily transmitted through several millimeters of skin, could be safely used to guide the surgeon. Laser irradiation can be controlled manually by the user or alternatively automatically controlled to prevent excessive or inappropriate thermal damage.

In the preferred embodiment the temperature of the target tissue is measured with a non-contact temperature sensor and the value displayed and used by the laser control unit to actively control the laser power. The preferred temperature sensor would be an infrared temperature sensor, but other conventional sensors may be used, such as fiber optic fluorescence temperature sensors, and thermocouple sensors.

In order to improve lysing efficiency, one embodiment of the device incorporates an ultrasound transducer into the hand piece that transmits ultrasound energy down the shaft. A lower frequency vibrating transducer could also be incorporated into the device to improve lysing.

For example, the shaft may be vibrated at frequencies lower than 5000 Hz.

In another embodiment, the recessed cutting segments of the device are driven by an electrosurgical RF generator to improve lysing and allow RF heating of tissue.

The present invention can be used to improve the efficacy and safety of face-lifting and is thus useful in a variety of cosmetic procedures. The forgoing and other objects, features, and advantages of the present invention will become apparent from the following description and accompanying drawings.

The disclosures of this publication and the disclosures of all other publications recited herein are incorporated by reference as if fully set forth herein.

BRIEF DESCRIPTION OF THE DRAWINGS

The accompanying drawings, which are incorporated into and form part of this disclosure, illustrate embodiments of the invention and together with the description, serve to explain the principles of the invention.

FIG. 5 shows a side view of attachment version of face-lift apparatus.

FIG. 6 shows top view of attachment version of face-lift apparatus.

FIG. 7 shows a side view of attachment version of face-lift apparatus and schematic diagram showing waveguide laser light delivery.

DETAILED DESCRIPTION OF THE INVENTION

The present invention provides a device that can be used by surgeons to provide quick and accurate face-lifting maneuvers that minimize the amount of tissue that has to be removed. The device is comprised of a hollow undermining shaft that can be easily positioned between dissection planes in tissue and then manipulated to separate tissue planes and lyse fibrous tissue, a laser light source and delivering means which delivers energy to the distal end of the shaft, a temperature sensor that monitors the tissue temperature, and control electronics that process temperature information to control the laser power for optimum tissue contraction. An optional secondary light source that is visible to the surgeon can be used to help visiualize the location of the laser exit window. Optionally the device can also use ultrasound energy delivered down the shaft to improve tissue lysing.

Figure 1:
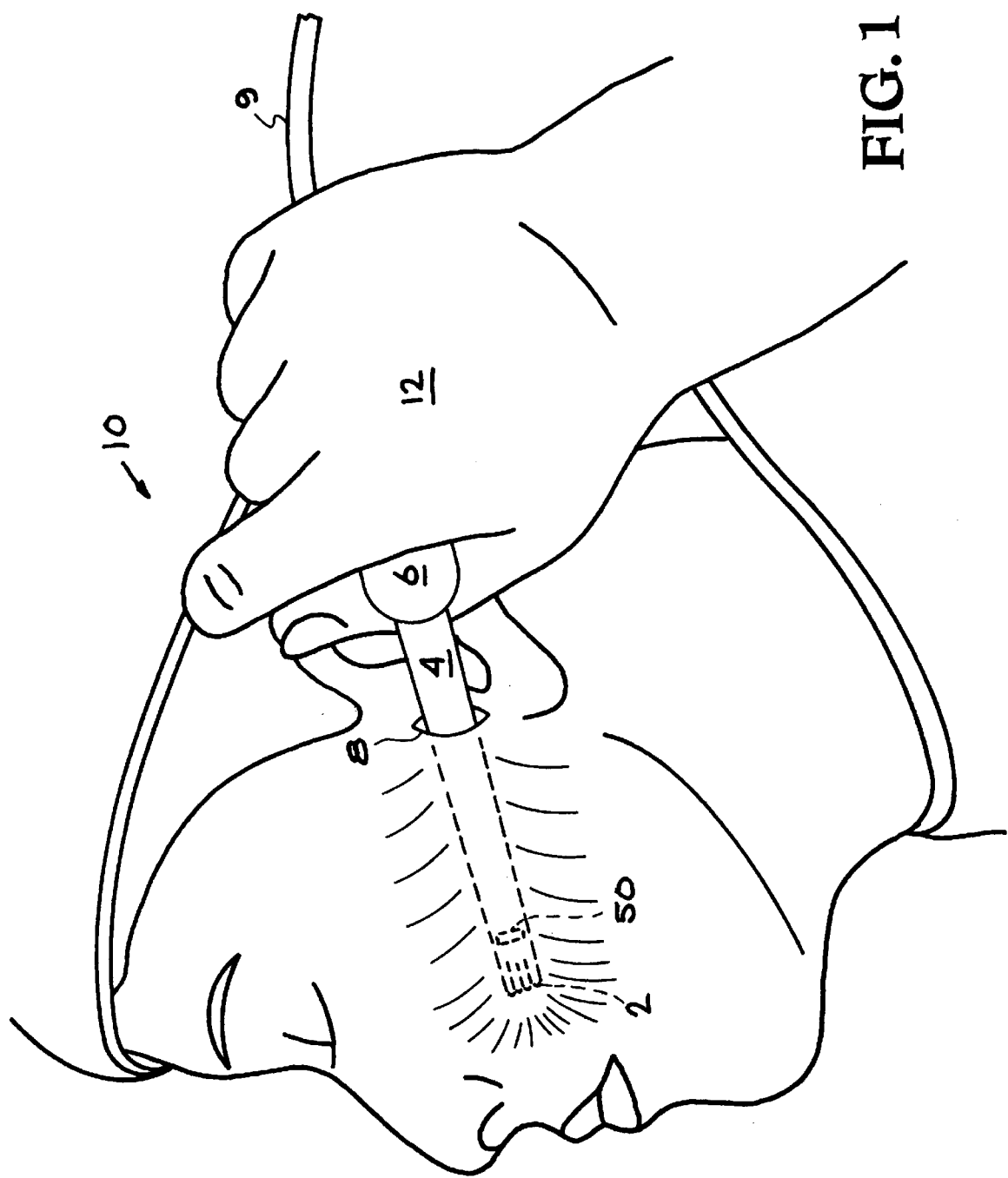
FIG. 1 shows present invention (and partial top view of face lift apparatus) in use.

FIG. 1 shows a partial top view of the face-lift apparatus 10 of the present invention as it is being used. The handle 6 of the apparatus 10 is gripped in the hand 12 of the user of the device. The shaft 4 with the special lysing tip 2 of the face-lift apparatus 10 is inserted through an opening at a suitable location on the face 8 of a patient. Dashed lines indicate the portion of the device hidden from view under the skin. Curved stretch lines indicate the upward force applied on the device 10 and therefore shaft 4 and therefore the overlying skin of the face. The apparatus may then be thrust forwardly while lifted forcefully by the operator to perform its function and maintain the plane of undermining. Window 50 (dashed and hidden from clear view in this representation) allows egress for laser light delivered to apparatus 10 via light delivery means contained in conduit 9. The conduit also contains the necessary electrical control wires necessary for device operation.

Figure 2:
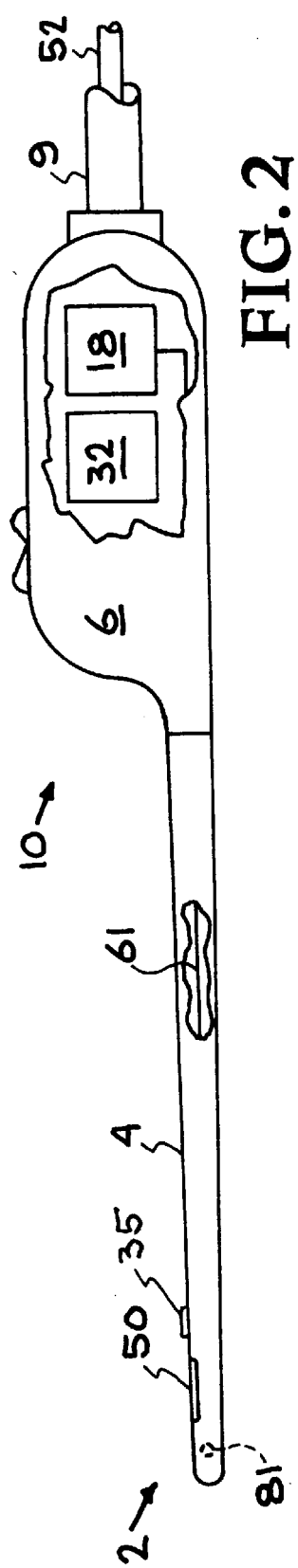
FIG. 2 shows a side view of face-lift apparatus attached to articulating arm or fiber optics.

FIG. 2 is a side view of the face-lift apparatus 10. The tip 2 may be slightly larger than the shaft 4. The tip 2 can be a separate piece that is secured to shaft 4 by a variety of methods such as a snap mechanism, mating grooves, plastic sonic welding, etc. Alternatively, in this model tip 2 can be integral or a continuation of shaft 4 made of similar metal or materials. The tip 2 may also be constructed of materials that are both electrically nonconductive and of low thermal conductivity; such materials might be porcelain, ceramics or plastics. An optional electrically conductive element 61 brings RF electrosurgical energy to metal or electrically conductive elements mounted in the recessions (see FIG. 3). The shaft 4 is tubular in shape or can be a somewhat flattened tube oblong in cross section and possibly geometric as well. The shaft 4 is made of metal with a hollow interior that can contain insulated wire or wires 61. Alternatively, the shaft 4 may be made of plastic that will act as its own insulation about wire or electrically conductive element 61. The optional electrically conductive element 61 internal to shaft 4 conducts electrical impulses or RF signals from an optional external power/control unit (such as a Valleylab Surgistat, Boulder, Colo.). Hidden from this direct view located at the most proximal portion of the groove is electrically conductive element 81 which effects forward lysing and is located at the terminus of conductive element 61. An optional temperature sensor 35 placed near the distal tip of the shaft is used to monitor the local temperature. This information can be used by the control electronics to control the energy delivered to the tip. An ultrasound transducer 32 can also be activated to transmit energy to the tip 2 and provide additional heating and improve lysing.

Figure 3:
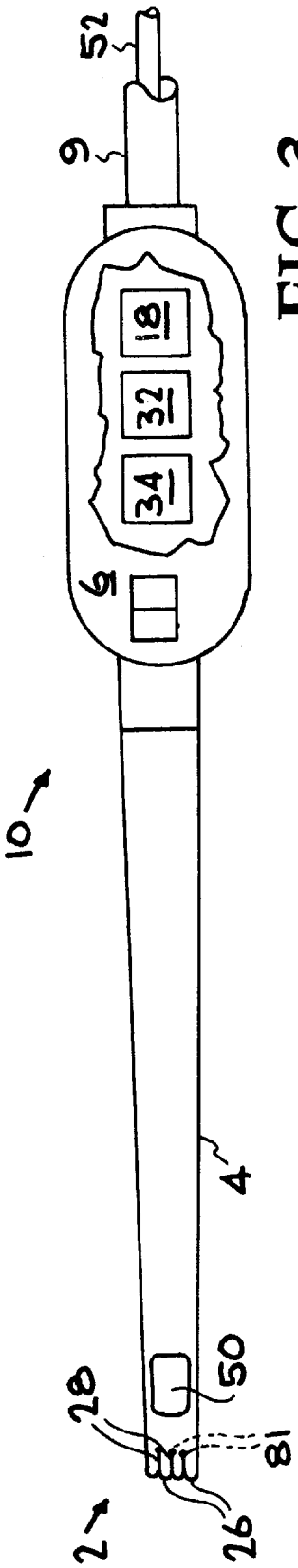
FIG. 3 shows top view of face-lift apparatus attached to articulating arm or fiber optics.

FIG. 3 is an enlarged plan or top view of the tip 2 as used in upper face-lift. This tip 2 shows four protrusions 26 and three recessions 28. The groove created by the tapering recessions may be noticeable up to one centimeter in length. The width of this tip varies between 12 mm to 20 mm and the thickness varies between 3 mm to 4 mm. Optical window 50 allows laser light to exit the shaft and irradiate tissue directly above. A light delivery means which can be an optical fiber or hollow waveguide 52 is contained in conduit 9. The conduit 9 can also be an articulating arm as is commonly used in surgical laser systems. Additional control wires and power are delivered to the handpiece in the conduit 9. The user can enable or disable the laser through control switch 55.

Figure 4:
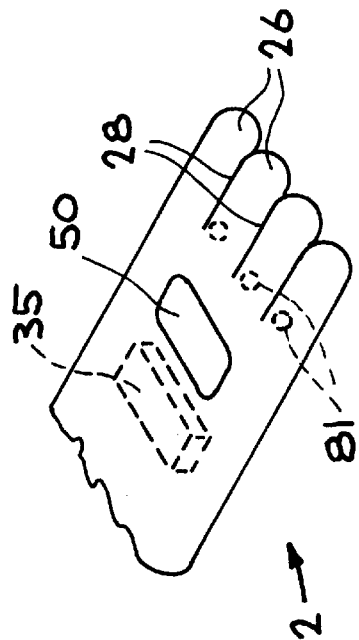
FIG. 4 shows off-center frontal view of tip of face-lift apparatus protrusions and recessions.

FIG. 4 shows an off-center frontal view of tip of face-lift apparatus protrusions and recessions. The tip 2 has four protrusions 26 and three recessions 28 in which are seated conductive elements 81. Window 50, allowing egress of laser light and temperature sensor 35 are also located on the tip and may be of varying sizes. The width of this tip varies between 5 mm and 10 mm while the thickness may vary between 2 mm to 4 mm. The tip, however, is not constrained by those dimensions.

FIG. 5 is a side view of the present invention 10 with detachable handle 78 that fits over exogenous laser source 77 such as a Sharplan flashscanner or a Coherent Ultrapulse. The hollow 44 of shaft 4 acts as a waveguide to allow laser to move to and exit from window 50 near tip 2. Window 50 allows egress for laser light delivered to apparatus 10.

FIG. 6 is a top view of the present invention 10 with detachable handle 78 that fits over exogenous laser source 77 such as a Sharplan flashscanner or a Coherent Ultrapulse. Shaft 4 acts as a waveguide to allow laser to move to and exit from window 50 that allows egress for laser light delivered to apparatus 10.

FIG. 7 is a cut-open view of the present invention 10 with detachable handle 78 wherein shaft 4 acts as a waveguide 44 to allow laser light 53 to move to and exit from window 50. An optical element 51 is used to reflect the laser light out through the window. In an alternative embodiment the waveguide 44 formed by the internal surface of the shaft 4 is replaced by a one or multiple optical fibers or hollow fibers waveguides. The preferred light delivery means depends on the wavelength of the laser used. Infrared light emitted by the heated tissue can also be collected through the window and used by an infrared detector to measure the tissue temperature.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

What is claimed is:

1. An apparatus for separating facial tissue planes and altering the tissue, comprising:
   a hollow shaft having a distal end and a proximal end;
   a plurality of protruding members on the distal end of the shaft separated by at least one interstitial lysing segment, wherein the lysing segment is recessed relative to the protruding members;
   at least one optical window in the shaft; and
   a means for delivering laser light from the proximal end of the shaft to the distal end so that light can be transmitted through the window to targeted tissue, wherein said plurality of protruding members extend from said distal end beyond said at least one optical window.

2. An apparatus as recited in claim 1, wherein the protruding members form a planar surface, and wherein the window is positioned such that the light transmitted through the window deviates from the planar surface by an angle of at least 5 degrees.

3. An apparatus as recited in claim 1, wherein the means for delivering laser light comprises at least one optical fiber in the shaft.

4. An apparatus as recited in claim 1, wherein the means for delivering laser light comprises a waveguide in the shaft.

5. An apparatus as recited in claim 1, wherein the hollow shaft has an inner surface, and wherein the means for delivering laser light comprises a reflective inner surface.

6. An apparatus as recited in claim 1, wherein the hollow shaft has an inner surface, and wherein the means for delivering laser light comprises a polished metal inner surface.

7. An apparatus as recited in claim 1, further comprising a temperature sensor.

8. An apparatus as recited in claim 7, wherein the temperature sensor comprises an infrared temperature sensor.

9. An apparatus as recited in claim 7, wherein the temperature sensor comprises an electronic temperature sensor at the distal end of the shaft.

10. An apparatus as recited in claim 7, wherein the temperature sensor comprises an optical fluorescence sensor.

11. An apparatus as recited in claim 7, wherein the temperature sensor comprises an optical fiber temperature sensor.

12. An apparatus as recited in claim 1, wherein at least one of the protruding members has an opening at the distal end.

13. An apparatus as recited in claim 12, further comprising at least one lumen extending through at least a portion of the shaft and terminating at the opening.

14. An apparatus as recited in claim 12, further comprising an optical window in the opening and means for delivering laser light from the proximal end of the shaft to the optical window in the opening.

15. An apparatus as recited in claim 1, further comprising means for delivering ultrasonic energy to the distal end of the shaft.

16. An apparatus as recited in claim 1, further comprising means for vibrating the shaft at frequencies lower than 5000 Hz.

17. An apparatus as recited in claim 1, further comprising control means for controlling the delivery of laser light to the distal end of the shaft.

18. An apparatus as recited in claim 17, further comprising a temperature sensor that senses the temperature at the distal end of the shaft, wherein the sensor sends a signal to the control means, and wherein the control means controls the delivery of laser light to the distal end to adjust the temperature.

19. An apparatus as recited in claim 17, further comprising a temperature sensor that senses the temperature of the laser heated tissue, wherein the sensor sends a signal to the control means, and wherein the control means controls the delivery of laser light to the distal end to adjust the temperature.

20. An apparatus as recited in claim 1, wherein at least one lysing segment comprises an electrode, and further comprising means for transmitting radiofrequency energy to the electrode.

21. An apparatus as recited in claim 1, wherein the thickness of the distal end of the shaft is less than about 1 cm and the width of the distal end is less than about 2 cm.

22. An apparatus as recited in claim 1, further comprising a source of laser light selected from the group consisting of a $CO_2$ laser, an erbium-YAG laser, and a holmium laser.

23. The apparatus of claim 1, wherein said distal end of the shaft is tapered.

24. The apparatus of claim 1, additionally including a means for delivering visible light from the proximal end of the shaft to the distal end so that light can be transmitted through the window and through tissue to show the location of the device.

25. An apparatus for separating facial tissue planes and altering the tissue, comprising:
   a hollow shaft having a distal end and a proximal end;
   a plurality of protruding members on the distal end of the shaft separated by at least one interstitial lysing segment, wherein the lysing segment is recessed relative to the protruding members, wherein said lysing segment comprises a cutting edge;
   at least one optical window in the shaft; and
   a means for delivering laser light from the proximal end of the shaft to the distal end so that light can be transmitted through the window to targeted tissue.

* * * * *